(12) United States Patent
Hibino et al.

(10) Patent No.: US 6,773,879 B2
(45) Date of Patent: Aug. 10, 2004

(54) PROCESS FOR OBTAINING PLANT DNA FRAGMENT AND USE THEREOF

(75) Inventors: Takashi Hibino, Suzuka (JP); Junko Koshiyama, Suzuka (JP)

(73) Assignee: Research Association for Reforestation of Tropical Forest, Tokyo (JP)

( * ) Notice: Subject to any disclaimer, the term of this patent is extended or adjusted under 35 U.S.C. 154(b) by 0 days.

(21) Appl. No.: 09/444,388

(22) Filed: Nov. 22, 1999

(65) Prior Publication Data

US 2002/0170084 A1 Nov. 14, 2002

(30) Foreign Application Priority Data

Nov. 25, 1998 (JP) .......................................... 10-333469

(51) Int. Cl.$^7$ ........................... C12Q 1/68; C12P 19/34; C07H 21/04
(52) U.S. Cl. .......................... 435/6; 435/91.1; 435/91.2; 536/24.3
(58) Field of Search .......................... 435/6, 91.1, 91.2, 435/320.1; 536/23.1, 24.3; 800/267

(56) References Cited

U.S. PATENT DOCUMENTS 5,436,142 A * 7/1995 Wigler et al. .............. 435/91.2

FOREIGN PATENT DOCUMENTS

JP            11146788 A     6/1999

OTHER PUBLICATIONS

Phillips et al. Plant Mol. Biol. vol. 24, pp 603–615, 1994.*
J. Kimble Frazer et al., Jounal of Immunological Methods, 207 (1997) pp. 1–12.*
Nainan et al., J. Vir. Methods, vol. 61, 1996, pp 127–134.*
Pinyopusarerk, K. ACIAR proceedings, No. 16, 1987, pp 147–148.*
Chang et al Science, vol. 266, Dec. 1994, p 1865.*
"Differential cloning of genomic DNA: Cloning of DNA with an altered primary structure by in–gel competitive reassociation," Proc. Natl. Acad. Sci. USA, vol. 87, pp. 6398–6402, Aug. 1990, Biochemistry.
"A genomic scanning method for higher organisms using restriction sites as landmarks," Proc. Natl. Acad. Sci. USA, vol. 88, pp. 9523–9527, Nov. 1991, Genetics.
"Cloning the Difference Between Two Complex Genomes," Science, vol. 259, Feb. 12, 1993, Nikolai Lisitsyn et al.

* cited by examiner

Primary Examiner—Jehanne Souaya
(74) Attorney, Agent, or Firm—Arent Fox Kintner Plotkin & Kahn, PLLC

(57) ABSTRACT

A process for obtaining a DNA fragment for a plant characterized by obtaining a polymorphic DNA fragment by genomic comparison using a plant material, and then using an RNA-derived labeled probe to select a DNA fragment therefrom; a gene coding for the DNA fragment; a promoter; expression vector and transformed plant obtained using the gene; as well as a breeding method for plants using the DNA fragment as a marker are provided.

7 Claims, 3 Drawing Sheets

Fig. 2
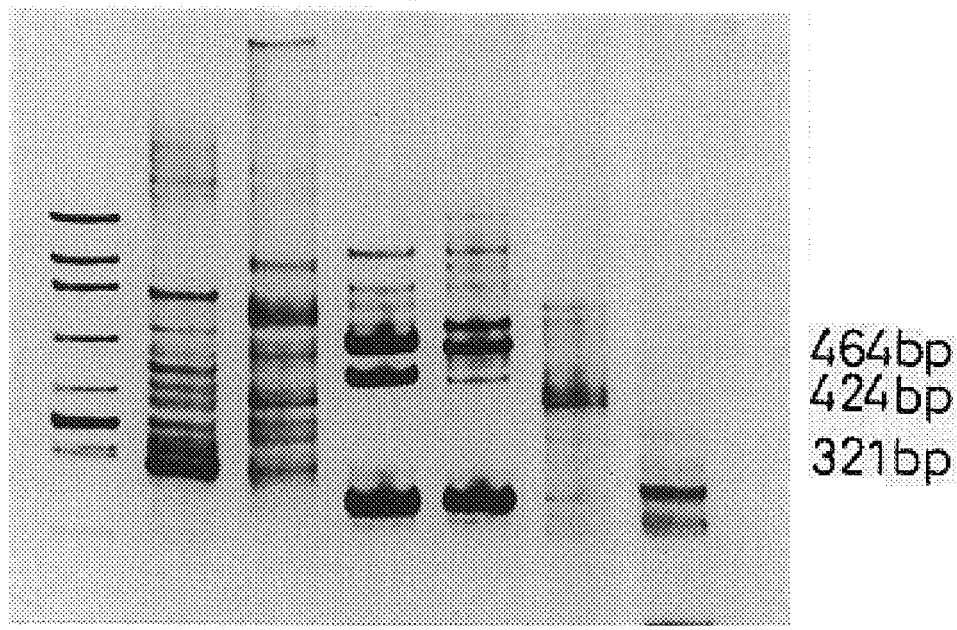
464bp
424bp
321bp
| tester | 2 | 2 | 2 | 2 | 2 | 2 |
| --- | --- | --- | --- | --- | --- | --- |
| driver | 2 | 4 | 2 | 4 | 2 | 4 |
| | BamHI | | EcoRI | | HindIII | |
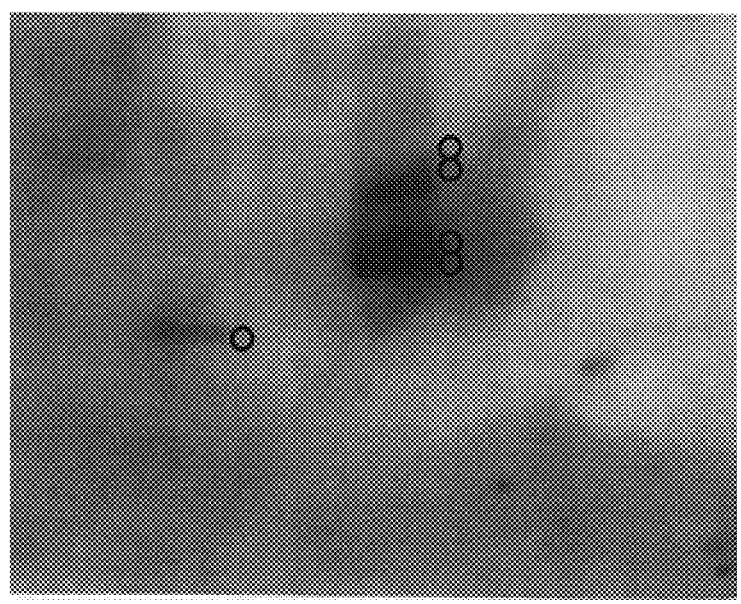

PROCESS FOR OBTAINING PLANT DNA FRAGMENT AND USE THEREOF

BACKGROUND OF THE INVENTION

1. Field of the Invention

The present invention relates to a process, for obtaining plant a DNA fragment, which employs genetic engineering and molecular genetics and to a process for breeding plants, particularly forest trees, by using the plant DNA fragment.

2. Related Art

A typical method for breeding plants begins with selection of suitable individual candidates, by a skilled technician, based on observational data and analytical data for phenotypes. After the suitable individual candidates have passed an inspection test, they are preserved as official suitable individuals (registered species). It is also important to create progeny with new phenotypes by crossbreeding between the selected suitable individuals. Many existing plant species have a history of repeated selection and crossbreeding steps, but in the case of forest trees as an example, because of their long growth period, they have a very short history of crossbreeding, and therefore results still remain to be obtained in the future.

Most traits useful as a target of for breeding are a combination of many physiological phenomena (for example, the nature and density of the material, in the case of forest trees). It is thought that each phenomenon is defined by a corresponding genetic information of the individual (its genome), and is expressed when necessary. However, it is very difficult to accurately determine the actual key physiological phenomena and elucidate the interconnecting systems for each phenomenon. For actual breeding, it is common to describe a genetic lineage extending for a number of generations, and examine the progeny to determine useful traits. In addition to phenotypes, the molecular biological analysis data for enzymes and nucleic acids have recently come to be treated as one of the traits. This has led to a drastic increase in the number of markers on the genome, though in a random manner. By applying such numerous markers to certain genetic lineages and statistically processing the resulting polymorphic data, it has become possible to create specific gene linkage maps for those lineages. It is thought that if the markers are appropriately dispersed and abundant on the map, markers strongly linked with certain phenotypes can theoretically be found; that is, it is believed that trait judgments can be made on the statistical genetic level. However, so far, no reports have been published which use such molecular markers as selection references. The following problem is thought to be one of the causes for this.

The genome includes portions for specific genetic information (coding regions) and other portions [non-coding regions (characterized by a primary structure whose function is unknown, repeating or recurrent nucleotide sequences)]. The non-coding regions constitute the greater part of the genome, while the coding regions are scattered throughout the entire genome. Almost all of conventionally used molecular markers (particularly those derived from DNA) are acquired randomly, and most molecular markers are derived from such non-coding regions. That is, the existing molecular markers are ones that are unrelated to individual phenotypes. Thus, the differences in the genome between individuals and between species result in cases where the molecular markers cannot be universally applied. Specifically, since heterozygosity is recognized between individuals in most species including forest trees, when existing markers are considered for breeding applications, it is highly possible that they will only be effective when a specific individual is used as the parent material. To circumvent this situation it has been desired to obtain breeding markers that allow judgment of useful types and can be universally utilized without being dependent on heterogeneity.

SUMMARY OF THE INVENTION

It is an object of the present invention to isolate a DNA fragment derived from a gene or a group of genes linked with expression of a trait that serves as a breeding marker for plants. It is another object of the invention to provide a breeding method that utilizes a promoter sequence obtained by analysis of the aforementioned DNA fragment and employs such a DNA fragment as selection markers for breeding.

BRIEF EXPLANATION OF THE DRAWINGS

The file of this patent contains at least one drawing executed in color. Copies of this patent with color drawing(s) will be provided by the Patent and Trademark Office upon request and payment of the necessary fee.

FIG. 2 shows the results of second genome subtraction (top row) and hybridization by the expression probe (bottom row) for acacia.

DETAILED DESCRIPTION

Figure 1:
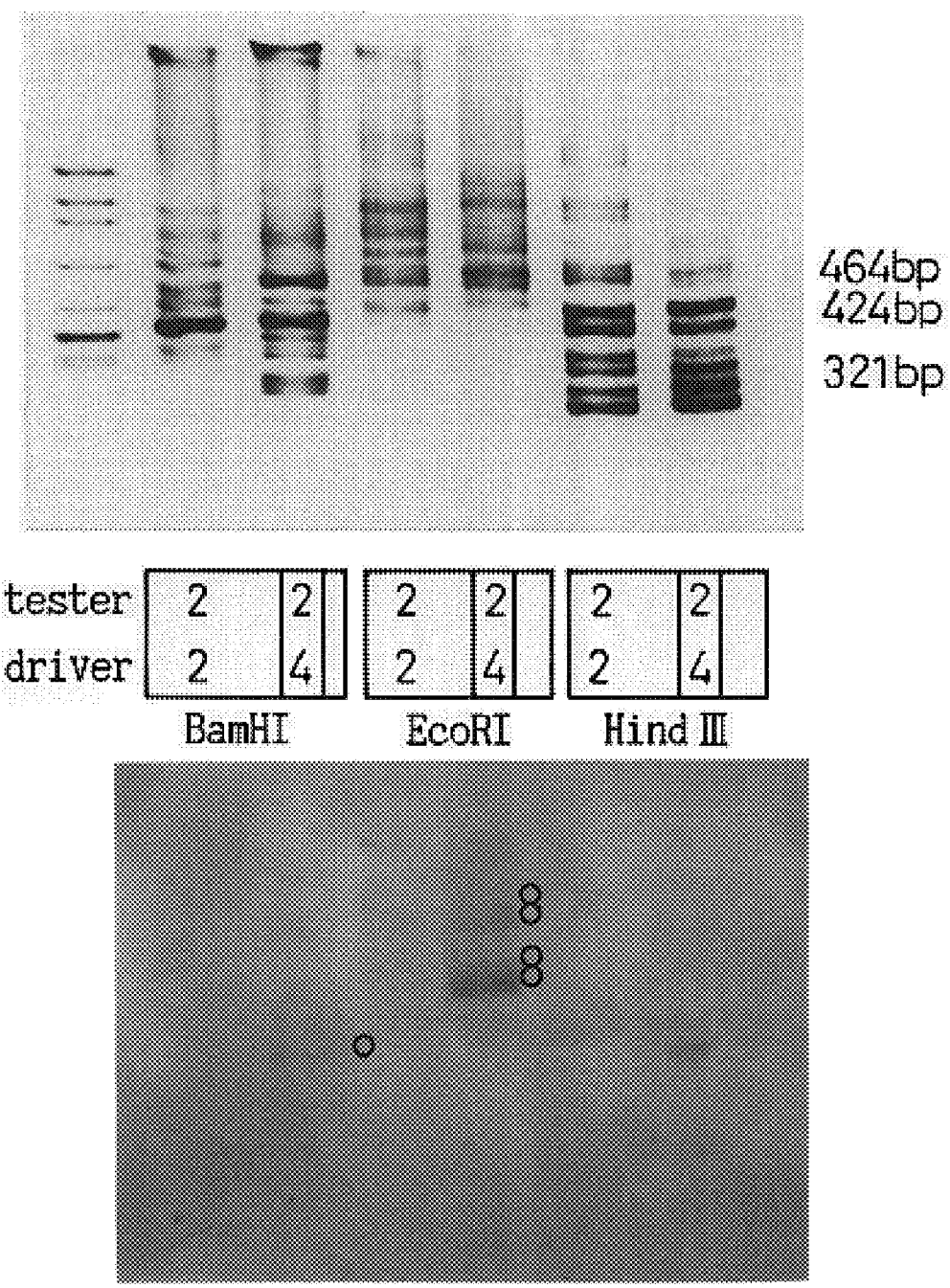
FIG. 1 shows the results of first genome subtraction (top row) and hybridization by the expression probe (bottom row) for acacia.
Figure 3:
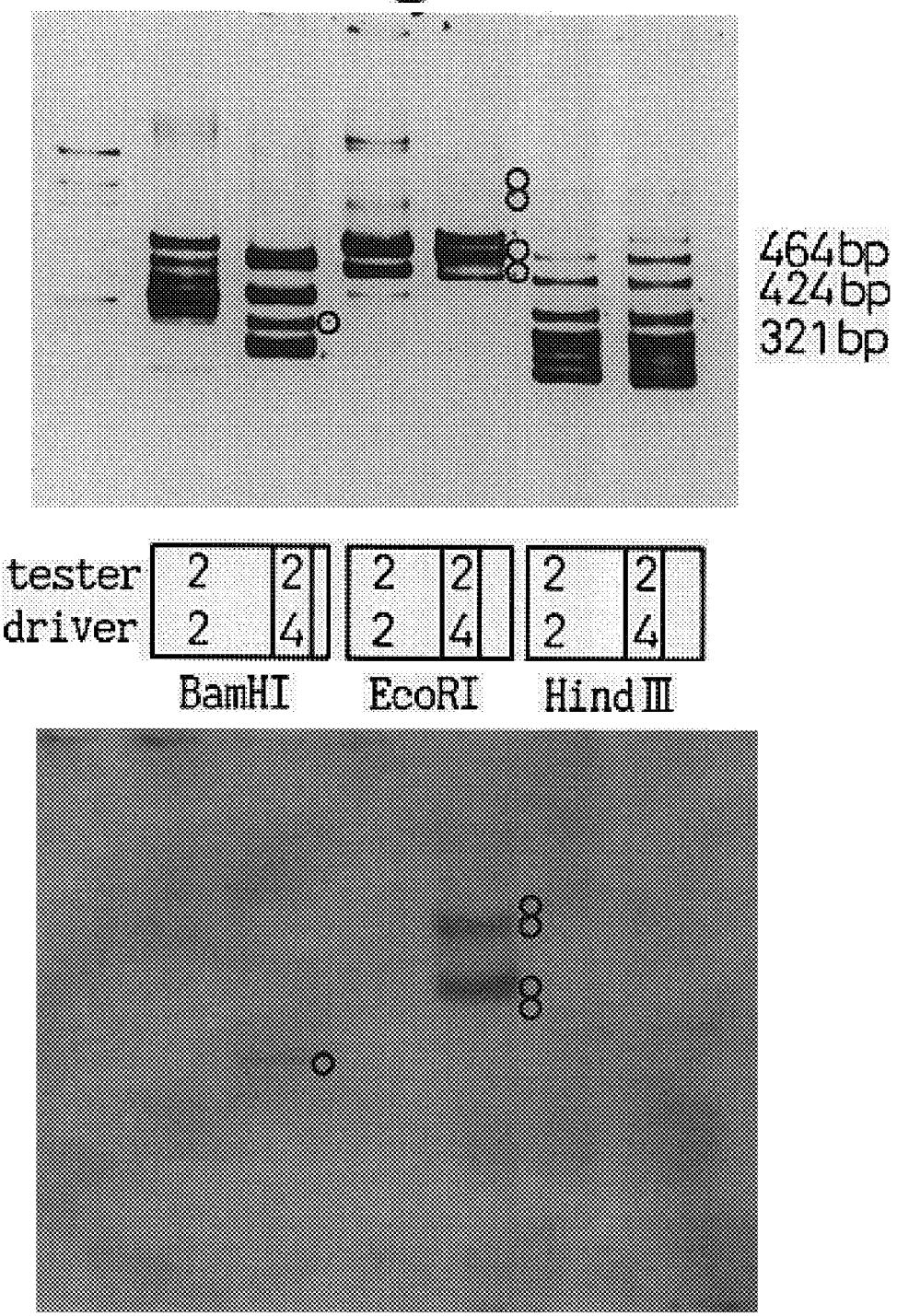
FIG. 3 shows the results of third genome subtraction (top row) and hybridization by the expression probe (bottom row) for acacia.

Accordingly the present invention provides a process for obtaining a plant DNA fragment, comprising the steps of (1) digesting plant DNA to form DNA fragments;

(2) subjecting the DNA fragments to genome subtraction to obtain polymorphic DNA fragments; and (3) screening the polymorphic DNA fragments using a RNA-derived labeled probe to obtain a desired plant DNA fragment.

The present invention further provides a DNA fragment obtainable according to the above-mentioned process.

The present invention also provides a gene comprising said DNA fragment.

The present invention further provides DNA comprising at least a part of said gene and having promoter activity.

The present invention moreover provides an expression vector comprising said DNA.

The present invention further provides a transgenic plant derived from a cell containing said expression vector or comprising said cells.

The present invention still more provides a process for breeding plant using, as an indicator, said DNA fragment.

DETAILED DESCRIPTION

The present inventors have researched to find a method for finding a gene or a group of genes linked with expression of a trait that serves as a target of breeding for plants. Variation in gene traits (high heterogeneity) is found between individuals of most plant species, unlike within artificially selected crop varieties, and therefore a considerable difference in phenotypic expression is usually expected. The inventors considered that a genome subtraction between individuals with large differences in phenotypic expression can make it possible to pick out differences in the genome.

As a specific means for genome subtraction the present inventors used representation difference analysis which is the genome subtraction method described by Lisitsyn et al., among the many methods disclosed in recent years. This method has allowed detection of many DNA fragments thought to originate from differences between genomes. These DNA fragments are obtained as a result which directly reflects the polymorphic sites found in both genomes, but most DNA fragments are thought to originate from non-coding regions which do not code for specific genes. Because it is difficult to analyze each of these separately, a method has been devised to eliminate them. This allows only DNA fragments originating from coding regions to be obtained.

The present inventors extracted total RNA from individuals to be analyzed and used it as a template to construct complementary DNA (cDNA), wherein a chemical labeling substance was employed for chemical labeling of a resulting cDNA. After fractionating the DNA fragments originating from differences between genomes by acrylamide gel electrophoresis, and then transfering the DNA fragments onto a nylon membrane, they were subjected to hybridization by a conventional method and a few positive DNA fragments were detected. These fragments were used as probes for hybridization to the genome according to a conventional method, and polymorphs reflecting differences between genomes were detected, thus completing the present invention.

The present invention will now be explained in further detail.

As one embodiment of the invention, a detailed explanation will now be given regarding the genome subtraction method of the invention and the method of utilizing the DNA fragments of the invention. Conventional methods necessary for gene recombination including digestion and ligation of DNA, transformation of E. coli, determination of gene nucleotide sequences and hybridization were carried out according to methods described in manuals supplied with commercially available reagents and apparatuses used for each procedure, and in laboratory manuals (for example, see T. Maniatis et al., Molecular Cloning, A Laboratory Manual, Cold Spring Harbor Laboratory, 1982).

(1) Selection of DNA fragments using genome subtraction and RNA-derived labeled probe The method of selection of DNA fragments using genome subtraction and an RNA-derived labeled probe according to the invention, and the DNA fragments obtained by the method, are characterized by first using genomic DNA derived from plant tissue, for example acacia plant tissue, to collect and select a DNA fragment by a genome subtraction method.

Genome subtraction methods include the in-gel competitive reassociation (IGCR) method (Yokota, H. et al., 1990), the restriction landmark genome scanning (RLGS) method (Hatada, I. et al., 1991) and the aforementioned representation difference analysis (RDA) method (Lisitsyn, N., 1993). For the RDA method, an analysis kit is commercially available from Takara Shuzo. Any of the above-mentioned methods allows detection of polymorphism using any desired plant genome as a starting material.

According to the invention, the method of obtaining a selected DNA fragment using genome subtraction and an RNA-derived labeled probe, and the DNA fragment thus obtained are finally characterized in that RNA is extracted from an individual used as a genome subtraction material with respect to the DNA polymorphic fragment obtained as described above, and for example digoxigenin-dUTP (DIG), a labeling substance by Roche Diagnostics, is mixed therewith to construct DIG-labeled cDNA to be used as a probe, by using reverse transcriptase by Pharmacia-Amersham, and hybridization between said DIG-labeled cDNA prove and the above-mentioned DNA fragments is carried out by a conventional method, after which positive bands are selected.

The DNA fragment obtained by the aforementioned steps is a DNA fragment selected using genome subtraction and an RNA-derived labeled probe. This method makes it possible to obtain a region originating from genomic difference between plants that are compared, and providing gene expression, i.e. a portion of the gene responsible for differences in traits between individuals that are compared.

The present invention establishes the presence of a gene regulating a phenotypic expression of interest and a process for isolating an indicator (DNA marker) for judging the presence of expression, and specifically, such marker can be used as selection marker for breeding.

Specific examples of DNA fragments obtained according to the invention will now be explained in detail by way of the examples given below.

(2) Isolation and analysis of promoter region derived from DNA fragment of the invention A DNA fragment obtained according to the invention is derived from a portion of a gene which is important in regulating a phenotypic expression of interest, and therefore the obtained DNA fragment can be analyzed to easily obtain a promoter region.

(3) Construction of transgenic plant having promoter region derived from DNA fragment of the invention introduced therein A coding region for any gene whose expression is desired in plant cells is linked downstream from a region containing at least a portion of the promoter region referred to above, in such a manner that the gene is transcribed in the forward direction, and it is incorporated into a transformation vector to construct recombinant DNA. Here, vectors that can be used for transformation will differ depending on the transformation method for the plant. For example, when the plant cells are transformed by the particle gun method, PEG method, electroporation method, etc., a plasmid vector that can be used for E. coli, such as Bluescript (Stratagene) may be used as the transformation vector. For transformation of plant bodies or plant cells by Agrobacterium infection, for example leaf disk method, infiltration method, etc., a binary vector such as pBI121 (Clontech) derived from Ti plasmid, for example, may be used.

The transformation of the plant cells can be accomplished by introduction of recombinant DNA into plant cells or a plant body by the particle gun method, PEG method, electroporation method or Agrobacterium infection method. The recombinant DNA introduced into plant cells is preferably integrated into the genomic DNA of the plant.

The transgenic plant or transformed plant cells can be stably maintained by incorporating a drug-resistant gene against kanamycin or hygromycin into the recombinant DNA used for transformation, and cultivating or culturing in an agar stationary medium or liquid medium containing the drug.

The promoter region derived from the DNA fragment of the invention can be introduced into plant bodies or plant cells of arboreous plants including dicotyledons such as *Arabidopsis thaliana* and tobacco, monocotyledons such as rice and corn, and poplar, eucalyptus, acacia, etc.

Many different foreign genes can be expected as genes under the control of DNA with promoter activity according to the invention. In particular, for plants wherein reporter gene-linked recombinant DNA has been introduced there are methods of use such as drug screening for improvement of trait to be bred, and this can also contribute to their industrial development.

EXAMPLES

The present invention will now be explained in further detail by way of Examples which, however, are in no way intended to restrict the invention.

Example 1

Selection of DNA Fragment Using Genome Subtraction and RNA-derived Labeled Probe Materials and Methods The RDA method was used as the genome subtraction method. The materials used were two sibling individuals of *Acacia auricaliformis* with a considerable plant size difference. These were seeded in the same time and cultivated in the same environment, and after 2 years passed a difference of about 50 centimeters was found in the tree height. A difference of about 2 centimeters was found in the root diameter. Genome subtraction was performed according to the method of Lisitsyn et al. using genomic DNA prepared from each leaf by a conventional method.

The total RNA was extracted from the two individuals. The extraction was conducted according to the method of Hiono et al. (Japanese Unexamined Patent Publication No. 8-80191). The invention of this extraction method relates to a method of extracting nucleic acid from arboreal plants characterized by treating arboreal plant tissue with a buffer solution containing a vanadyl ribonucleoside compound and trimethylammonium hexadecyl bromide.

The obtained RNA and an oligonucleotide [SEQ ID. No.1 of the Sequence List (5'-GGGAGGCCCCTTTTTTTTTTTTTTTT-3')] were used to construct single-stranded cDNA using a cDNA synthesis kit by Pharmacia. A chain of a few tens of guanine was linked to the 5' end of the obtained single-stranded cDNA using terminal deoxynucleotidyl transferase and deoxyguanine by Takara Shuzo.

Next, two different oligonucleotides [SEQ ID. No.1 of the Sequence List and SEQ ID. No.2 of the Sequence List (5'-AAGGAATTCCCCCCCCCCCCCC-3')] were used as primers to amplify the cDNA fragment by the PCR method. Digoxigenin-dUTP (DIG), a labeling substance by Roche Diagnostics was mixed with the amplification reaction solution to chemically label the amplified DNA to make a cDNA-derived expression probe.

The DNA fragment obtained after subtraction by the method of Lisitsyn et al. was fractionated by acrylamide gel electrophoresis, and transferred to a nylon membrane by Roche Diagnostics using a nucleic acid transfer apparatus by Nihon Eido to make subtraction filters. The aforementioned expression probe was used for hybridization on these filters by a conventional method.

The positive DNA fragments were subcloned using a TA cloning kit by Invitrogen, and their nucleotide sequences were identified by the dideoxy method.

Results

If subtraction is sufficiently effective, there will theoretically be no DNA fragments remaining when the same genome is used as the material. Actually, however, many DNA fragments were found. This is attributed to slight differences in the genome, and when organisms with heterogeneity are used as materials, these must be eliminated somehow. As one means of achieving this, the present inventors attempted detection of intrinsic heterovariation by subtraction within the same individual. That is, by using this as a control experiment, a modification was made to allow accurate judgement of the genome subtraction between the original individuals of interest, by contrast with the subtraction results between the individuals of interest. This may be considered as an essential condition when using materials with high heterogeneity, since it can also be reflected even in hybridization using expression probes.

Subtraction was performed between the 2 individuals in this experiment to finally obtain six DNA fragments (see FIG. 1).

FIG. 1 shows the results for genome subtraction (top row) and hybridization by the expression probe (bottom row) for acacia.

FIG. 1 shows the results for the individual #2 (acacia individual with good growth) as a member to be subtracted (indicated as "tester") and the individual #4 (acacia individual with poor growth) as a member subtracting (indicated as "driver"). The subtraction was performed 3 times in a row according to a conventional subtraction method, and three restriction enzymes (BamHI, EcoRI, HindIII) were used. The columns where both the tester and the driver are individual #2 are where the subtraction was within the same individual as a control experiment for comparison. The circles in FIG. 1 indicate DNA fragments selected by subtraction that were judged as being complementary with the experiment probe.

The obtained DNA fragments were subjected to Southern analysis against the genome of the two acacia species used in the experiment, to confirm polymorphism.

According to the invention there has been established a method whereby a polymorphic DNA fragment is obtained from a plant by genome subtraction, and then an RNA-derived labeled probe is used to select DNA fragment therefrom. It has thereby become possible to judge the presence or absence of phenotypic expression specific to an individual, and to obtain universal breeding markers without being dependent on heterogeneity in the genome. In addition, it is possible to artificially modify expression by utilizing the gene coding for the DNA fragment obtained by the present process or their promoter regions.

What is claimed is:

1. A method for identifying DNA for polymorphic forest tree plants, comprising the steps of:
   a) selecting two sibling individuals of a forest tree plant having different phenotypes;
   b) obtaining genomic DNA from the two individuals;
   c) selecting DNA fragments by an inter-individual genome subtraction method using the genomic DNA from the two individuals;
   d) providing a labeled cDNA probe derived from all mRNA obtained from the two individuals, wherein the cDNA is selected and amplified by oligonucleotide primers in a polymerase chain reaction;
   e) fractionating the DNA fragments obtained by the genome subtraction of step c) and screening the DNA fragments with the RNA-derived labeled probe of step d);
   f) performing intra-individual subtraction with genomic DNA from one of the two individuals; and
   g) comparing the DNA fragments of steps e) and f) to exclude the DNA fragments containing intra-individual polymorphisms and identifying the DNA fragments that are polymorphic between the individuals.

2. The method of claim 1, wherein the forest tree is Acacia.

3. The method of claim 2, wherein the Acacia is a species *Acacia auriculiformis*.

4. The method of claim 1, wherein the genome subtraction method is representation difference analysis.

5. The method of claim 1, wherein the labeled cDNA is labeled with digoxigenin.

6. The method of claim 1, wherein the oligonucleotide primers consist of the sequences of SEQ ID NO: 1 and SEQ ID NO: 2.

7. The method of claim 1, wherein the DNA fragments are fractionated by acrylamide gel electrophoresis.

* * * * *

SEQUENCE LISTING

<160> NUMBER OF SEQ ID NOS: 2

<210> SEQ ID NO 1
<211> LENGTH: 26
<212> TYPE: DNA
<213> ORGANISM: Artificial Sequence
<220> FEATURE:
<223> OTHER INFORMATION: Synthetic primer for PCR

<400> SEQUENCE: 1
gggaggcccc ttttttttt tttttt                                    26

<210> SEQ ID NO 2
<211> LENGTH: 22
<212> TYPE: DNA
<213> ORGANISM: Artificial Sequence
<220> FEATURE:
<223> OTHER INFORMATION: Synthetic primer for PCR

<400> SEQUENCE: 2
aaggaattcc cccccccccc cc                                       22